United States Patent
Rademacher et al.

(10) Patent No.: US 9,605,874 B2
(45) Date of Patent: Mar. 28, 2017

(54) PHASE CHANGE HEAT PACKS

(71) Applicant: Warmilu, LLC, Ann Arbor, MI (US)

(72) Inventors: Rachel Lynn Rademacher, Holt, MI (US); Weidong Chen, Ann Arbor, MI (US); Grace Hsia, Troy, MI (US)

(73) Assignee: Warmilu, LLC, Ann Arbor, MI (US)

( * ) Notice: Subject to any disclaimer, the term of this patent is extended or adjusted under 35 U.S.C. 154(b) by 430 days.

(21) Appl. No.: 14/212,498

(22) Filed: Mar. 14, 2014

(65) Prior Publication Data

US 2014/0261380 A1     Sep. 18, 2014

Related U.S. Application Data

(60) Provisional application No. 61/798,048, filed on Mar. 15, 2013.

(51) Int. Cl.
*F24J 1/00* (2006.01)
*A61F 7/03* (2006.01)
(Continued)

(52) U.S. Cl.
CPC .............. *F24J 1/00* (2013.01); *A61F 7/0097* (2013.01); *A61F 7/03* (2013.01); *F28D 20/026* (2013.01); *F28D 20/028* (2013.01); *H05B 1/025* (2013.01); *H05B 3/36* (2013.01); *H05B 3/54* (2013.01); *A61F 2007/0231* (2013.01); *A61F 2007/0233* (2013.01); *A61F 2007/0249* (2013.01);
(Continued)

(58) Field of Classification Search
CPC ... F24J 1/00; A61F 7/03; A61F 7/0097; A61F 2007/0293; A61F 2007/0231; A61F 2007/0233; A61F 2007/0249; A61F 2007/0292; F28D 20/026; F28D 20/028; Y02E 60/145; H05B 1/025; H05B 3/54; H05B 3/36
See application file for complete search history.

(56) References Cited

U.S. PATENT DOCUMENTS 3,854,156 A   12/1974  Williams
3,951,127 A   4/1976   Watson et al.
(Continued)

FOREIGN PATENT DOCUMENTS

EP    0 437 331 B1    10/1994
EP    2 112 451 B1    1/2012
(Continued)

OTHER PUBLICATIONS

Keinänen, Mikko, Latent Heat Recovery From Supercooled Sodium Acetate Trihydrate Using A Brush Heat Exchanger, Master's Thesis, Aug. 30, 2007, Department of Mechanical Engineering, Helsinki University of Technology.

*Primary Examiner* — Alfred Basichas
(74) *Attorney, Agent, or Firm* — Young Basile Hanlon & MacFarlane, P.C.

(57) ABSTRACT

A heat pack includes a housing, a first phase change material (PCM) that is contained in the housing, and a thermal storage buffer that is contained in the housing. The thermal storage buffer includes a second PCM. An initiator is in operative contact with the first PCM. Activation of the initiator causes crystallization of the first PCM, and the first PCM cooperates with the thermal storage buffer to provide heat at a predetermined temperature range upon crystallization of the first PCM.

12 Claims, 5 Drawing Sheets

(51) Int. Cl.
*F28D 20/02* (2006.01)
*A61F 7/00* (2006.01)
*H05B 1/02* (2006.01)
*H05B 3/36* (2006.01)
*H05B 3/54* (2006.01)
*A61F 7/02* (2006.01)

(52) U.S. Cl.
CPC .............. *A61F 2007/0292* (2013.01); *A61F 2007/0293* (2013.01); *Y02E 60/145* (2013.01)

(56) References Cited

U.S. PATENT DOCUMENTS

| | | | |
|---|---|---|---|
| 4,077,390 A * | 3/1978 | Stanley | .......... A61F 7/03 126/263.04 |
| 4,154,106 A | 5/1979 | Inoue et al. | |
| 4,425,488 A | 1/1984 | Moskin et al. | |
| 4,455,358 A | 6/1984 | Graham et al. | |
| 4,563,404 A | 1/1986 | Bahary | |
| 4,712,263 A | 12/1987 | Pronzinski | |
| 4,856,294 A | 8/1989 | Scaringe et al. | |
| 4,872,422 A | 10/1989 | Della Vecchia | |
| 5,058,563 A | 10/1991 | Manker | |
| 5,243,724 A | 9/1993 | Barnes | |
| 5,339,796 A | 8/1994 | Manker | |
| 5,415,222 A | 5/1995 | Colvin et al. | |
| RE35,586 E | 8/1997 | Manker | |
| 6,185,744 B1 | 2/2001 | Poholski | |
| 6,298,907 B1 | 10/2001 | Colvin et al. | |
| 6,615,906 B1 | 9/2003 | Fieback et al. | |
| 6,652,771 B2 | 11/2003 | Carn | |
| 6,755,852 B2 | 6/2004 | Lachenbruch et al. | |
| 6,855,410 B2 | 2/2005 | Buckley | |
| 6,931,875 B1 | 8/2005 | Allen et al. | |
| 7,727,267 B2 | 6/2010 | Lachebruch | |
| 7,744,640 B1 | 6/2010 | Faries, Jr. et al. | |
| 8,257,416 B2 | 9/2012 | VanderSchuit | |
| 8,257,417 B2 | 9/2012 | Chen et al. | |
| 8,333,903 B2 | 12/2012 | Rolland et al. | |
| 8,443,623 B2 | 5/2013 | Matta et al. | |
| 2002/0113101 A1 | 8/2002 | Skillern | |
| 2003/0109910 A1 | 6/2003 | Lachenbruch et al. | |
| 2004/0186541 A1 | 9/2004 | Agarwal et al. | |
| 2004/0194915 A1 | 10/2004 | Belady et al. | |
| 2004/0199998 A1 | 10/2004 | Shinner | |
| 2004/0260369 A1 | 12/2004 | Schock et al. | |
| 2006/0036304 A1 | 2/2006 | Cordani et al. | |
| 2006/0057917 A1 | 3/2006 | Horowitz et al. | |
| 2007/0055330 A1 | 3/2007 | Rutherford | |
| 2007/0148447 A1 | 6/2007 | Amundson et al. | |
| 2007/0284356 A1 | 12/2007 | Findlay | |
| 2008/0072453 A1 | 3/2008 | Mizrahi | |
| 2008/0149674 A1 | 6/2008 | Hiniduma-Lokuge | |
| 2009/0036665 A1 * | 2/2009 | Domingo | ............... B01L 3/502 536/25.41 |
| 2010/0010599 A1 | 1/2010 | Chen et al. | |
| 2010/0137953 A1 | 6/2010 | Stein | |
| 2011/0024433 A1 | 2/2011 | Rolland et al. | |
| 2011/0190856 A1 | 8/2011 | Burke et al. | |
| 2012/0241122 A1 | 9/2012 | Xiang et al. | |
| 2012/0305231 A1 | 12/2012 | Liang et al. | |
| 2012/0330388 A1 | 12/2012 | Chen et al. | |

FOREIGN PATENT DOCUMENTS

| | | |
|---|---|---|
| EP | 1 979 697 B1 | 3/2012 |
| WO | 2007117159 A1 | 10/2007 |
| WO | 2010092393 A1 | 8/2010 |

* cited by examiner

PHASE CHANGE HEAT PACKS

CROSS-REFERENCE TO RELATED APPLICATIONS

This application claims the benefit of U.S. Provisional Application Ser. No. 61/798,048, filed on Mar. 15, 2013, which is incorporated herein in its entirety by reference.

BACKGROUND

This disclosure relates generally to the field of nonelectric reusable heat sources.

Devices known as heat pads and heat packs have been long used for many different applications. As one example, such devices are commonly used for physical therapy or pain management, by applying heat to a localized portion of a person's body. As another example, such devices are commonly used to extend the period of time that an individual can spend comfortably outside during cold weather conditions.

There are several basic types of heat pads and heat packs, each employing a different technology. Electrical heating pads can provide heat at a desired temperature for an indefinite period of time, but require an electrical power source. Some heating pads and heating packs use a material having a high specific heat capacity to provide heat for a limited period of time immediately after being heated. A hot water bottle is an example of a device that uses a high specific heat material, namely water, to provide heat immediately after the water is heated and placed in the bottle.

Chemical heat packs are known that remain at room temperature until activated, causing an exothermic reaction that lasts for a period of time after activation. Some chemical heat packs can be used only once, and are non-reusable. An example of a single-use chemical heat pack employs a binary mixture where a chemical reaction is initiated by mixing the components of the binary mixture. Other chemical heat packs are reusable. One common type of reusable chemical heat pack utilizes a phase change material, such as a supercooled solution of sodium acetate ($CH_3COONa$) in water, where the phase change material crystallizes exothermically when activated. The heat pack is prepared for subsequent use by melting the phase change material, such as by immersing the heat pack in hot water.

SUMMARY

Phase change heat packs are described herein.

One aspect of the disclosed embodiments is a heat pack that includes a housing, a first phase change material (PCM) that is contained in the housing, and a thermal storage buffer that is contained in the housing. The thermal storage buffer includes a second PCM. An initiator is in operative contact with the first PCM. Activation of the initiator causes crystallization of the first PCM, and the first PCM cooperates with the thermal storage buffer to provide heat at a predetermined temperature range upon crystallization of the first PCM.

Another aspect of the disclosed embodiments is a heat pack that includes a housing in the form of a sealed flexible container. A first phase change material (PCM) is contained in the housing. The first PCM includes sodium acetate. A thermal storage buffer is contained in the housing. The thermal storage buffer includes a second PCM in the form of a paraffin wax. An initiator is in operative contact with the first PCM. The initiator includes a stainless steel member that, when activated by physical manipulation of the stainless steel member, provides nucleation sites for the first PCM to cause crystallization of the first PCM. Crystallization of the first PCM provides heat at a first temperature. The heat provided by the first PCM melts the second PCM of the thermal storage buffer at a second temperature such that the second PCM of the thermal storage buffer absorbs part of the heat provided by first PCM. The first PCM cooperates with the thermal storage buffer to provide heat at a predetermined temperature range from 36 to 44 degrees Celsius upon crystallization of the first PCM. The first temperature is above the predetermined temperature range and the second temperature is within the predetermined temperature range.

BRIEF DESCRIPTION OF THE DRAWINGS

The description herein makes reference to the accompanying drawings wherein like referenced numerals refer to like parts throughout several views and wherein.

DETAILED DESCRIPTION

This disclosure relates to a nonelectric, reusable heat system which is regulated by an initiator and other additives that help the heat system maintain a controlled temperature for a controlled duration of time. Warming technology can often be used in cold weather to extend the period of time an individual can spend comfortably outside. One embodiment of the heat system can be used in an infant warmer, but the heat system can also be used in clothing, shoes, outdoor recreational gear, and other embodiments.

Figure 1:
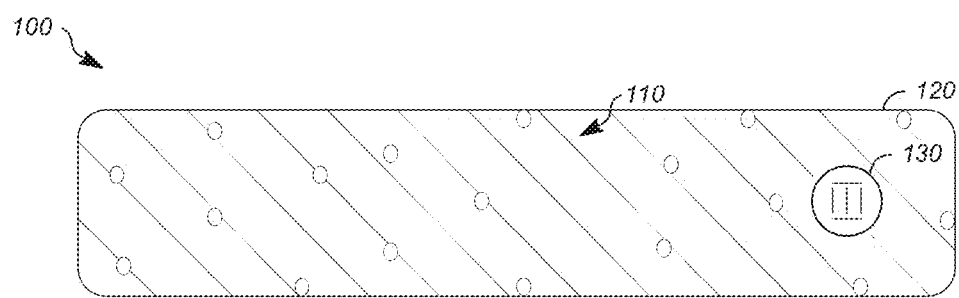
FIG. 1 is an illustration showing a heat pack according to a first example.

FIG. 1 shows a system for temperature regulation, which is referred to herein as a heat pack 100. The heat pack 100 includes a heat source 110 that is contained within a housing 120, which may also be referred to herein as an enclosure or a container.

The housing 120 is formed from a pliable material such as, for example, polyethylene. The housing 120 can be manufactured in numerous shapes, including cylindrical, in order to contain the heat source. The heat source 110 can be contained in any shape, be it a cylindrical, spherical, cubic, and the like. It may also be contained in a package enclosing multiple packs in one.

The heat source 110 includes a first phase change material (PCM). The first phase change material can be an inorganic phase change material, such as an inorganic salt. The first PCM provides heat during an exothermic phase change, such as a phase change from a liquid state to a solid state by crystallization of the material. In particular, the first PCM can be a material that is able to maintain a supercooled liquid stated while contained within the housing 120. As will be explained herein, the phases change can be initiated by providing nucleation sites for crystallization of the first PCM. As an example, the first PCM can be $NaCH_3COO \times 3H_2O$ (sodium acetate trihydrate and water mixed in a supersaturated solution), which has a melting point of 58° C. and heat of fusion ($\Delta H_{fus}$) of 252 kJ/kg (60.3 cal/g).

The heat source 110 can also include a thermal storage buffer. The thermal storage buffer can be used to regulate the temperature and control over the heat generation of the heat pack 100 during the exothermic phase change of the first PCM of the heat source 110. In particular, the first PCM and the thermal storage buffer can cooperate to control the temperature of the heat pack 100 within a predetermined range. In addition, the thermal storage buffer can store heat provided by the exothermic phase change of the first PCM, and continued to release the stored heat after the first PCM has cooled.

The thermal storage buffer can be or include a second PCM. The second PCM can be an organic material that melts (i.e. changes phase from solid to liquid) at a certain temperature, which can limit or otherwise regulate the maximum temperature, as a portion of the heat generated by the exothermic phase change of the first PCM will be absorbed by the second PCM, thus controlling the overall temperature of the heat pack 100. Thus, the first PCM of the heat source 110 can provide heat at a first temperature that is higher than the predetermined temperature range for the heat pack 100 during crystallization of the first PCM, and the second PCM can have a melting point at a second temperature that is within the predetermined temperature range such that the second PCM of the thermal storage buffer moderates the heat generated by the first PCM by melting at the second temperature.

As an example, the second PCM can be paraffin wax. Paraffin wax is just one example of an organic phase change material that can be utilized as the thermal storage buffer of the heat source 110. Other emollients and materials that may be used as the thermal storage buffer of the heat source 110, such as Dermowax ISB, Finsolv 116, or the like.

The heat generated by the heat source 110 can be further regulated by the ratio of the first PCM to water. In one implementation, the heat source 110 can include a solution of sodium acetate trihydrate and water in a 2:1 ratio, which reaches a temperature of 57 degrees Celsius within seconds of initiation. In another implementation, the heat source 110 can include a solution of sodium acetate trihydrate and water in a 1:1 ratio, which reaches 36-38 degrees Celsius within seconds of initiation. These temperatures can be tuned using varying compositions of sodium acetate, other additives, and the like to get a desired quantity of heat delivered at a particular temperature.

Figure 9:
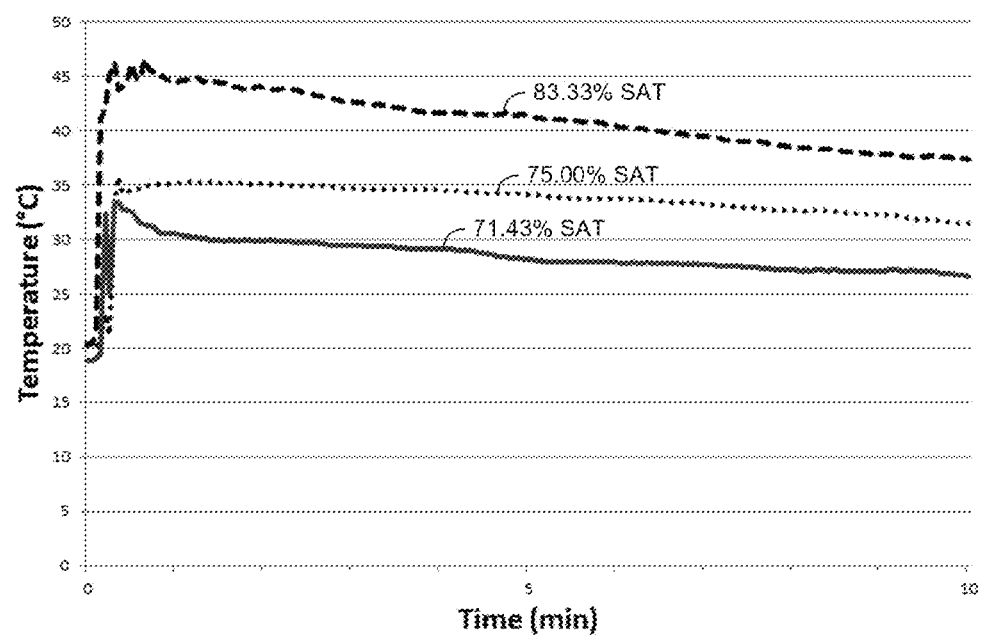
FIG. 9 is a graph showing the temperatures of three different sodium acetate trihydrate solutions after crystallization was initiated.

FIG. 9 is a graph showing temperatures generated in an experiment in which the first PCM is sodium acetate trihydrate. Three sodium acetate trihydrate (SAT) solutions were prepared, at 83.33%, 75.00% and 71.43% sodium acetate trihydrate, respectively, in water. The 83.33% SAT solution was prepared with 30 grams of sodium acetate trihydrate in 6 milliliters of water, and reached a peak temperature of 46.2 degrees Celsius. The 75.00% SAT solution was prepared with 30 grams of sodium acetate trihydrate in 10 milliliters of water, and reached a peak temperature of 35.3 degrees Celsius. The 71.43% SAT solution was prepared with 30 grams of sodium acetate trihydrate in 12 milliliters of water, and reached a peak temperature of 33.5 degrees Celsius.

The heat source 110 can produce heat in a predetermined temperature range. For example, the predetermined temperature range for the heat source 110 can be from 30-60 degrees Celsius. The heat source 110, in certain implementations, can be tuned to provide heat in a more specific temperature range, such as by inclusion of the second PCM in the heat source 110. The inorganic PCM controls the max temperature by melting at the advised peak temperature in addition the temperature control provided by different ratios of SAT or other heat generating solutions to water. As one example, the heat source 110 can be 60-95% inorganic salt (e.g. sodium acetate trihydrate), 5-30% water, and 5-35% heat buffer.

In another experiment, a solution was prepared using 30 grams of sodium acetate trihydrate as the first PCM, 0.05 grams of wax as the second PCM, and 6 milliliters of water. This solution reached a peak temperature of 43.325 degrees Celsius, showing that a small amount of the second PCM is able to reduce the peak temperature of the solution, as compared to the 46.2 degree peak temperature achieved by the 83.33% SAT solution as described above. Thus, the heat source 110 can be 60-95% inorganic salt (e.g. sodium acetate trihydrate), 5-30% water, and 0.1-35% heat buffer.

The heating characteristics of the heat source 110 can be tuned by adjusting the percent weights of the first PCM, the second PCM, and water, as discussed above. Good results have been obtained using a solution of 75-80% sodium acetate trihydrate, 10-15% paraffin wax, and 5-10% water, all by percent weight. As an example, a solution of approximately 78% sodium acetate trihydrate, 13% paraffin wax, and 9% water, when crystallized, produces temperatures of 36.5-37.5 degrees Celsius for an extended period of time.

An initiator 130 is contained in the housing 120 and is in operative contact with the first PCM of the heat source 110. To activate the heat source 110, this example of the initiator 130 is physically manipulated, such as being bent or flexed. The initiator 130 can be a corrosion resistant and slightly curved disk and flexing initiates the reaction by exposing slits or ridges in some embodiments to create sites for nucleation. The activator disk material of construction can be stainless steel or the like. The sodium acetate trihydrate crystals of the first PCM of the heat source 110 form a meta-stable reaction. By flexing the initiator 130, the bending opens up new areas and exposes defects to the first PCM of the heat source 110. When a defect is introduced to the system it becomes a potential site of nucleation for a seed crystal of the first PCM of the heat source 110. At this site, a seed crystal of is nucleated and triggers the nucleation of other crystals of the first PCM of the heat source 110, such as sodium acetate crystals. Thus, the first PCM crystallizes in response to activation of the initiator 130.

By incorporating an inorganic PCM such as the first PCM in the heat source 110, the heat pack 100 provides a nonelectric, temperature-controlled, and reusable source of heat. Thus, the heat pack 100 can be used to create a controlled temperature control system. As examples, the heat pack 100 could be used to provide warmth in an infant warming blanket to thermoregulate an infant, to warm up a car engine, or in many other applications.

In use, the heat pack 100 is typically at room temperature prior to activation, and the first PCM is in its liquid state. The initiator 130 is then activated, such as by flexing, the begin crystallization of the first PCM of the heat source 110. As first PCM of the heat source 110 provides heat, the second PCM is melted, thereby absorbing and storing heat to regulate the temperature of the heat pack 100 within the predetermined temperature range and to extend the period of time over which heat is provided by the heat pack 100. After use, the first PCM of the heat source 110 is in its solid state. The heat pack 100 is then recharged by melting the first PCM of the heat source 110. As an example, the heat pack 100 can be placed into boiling water for 10-15 minutes, which melts the solidified first PCM and puts it back into the supersaturated liquid state. Then the heat source 110 material can be activated again by the initiator 130 to generate another cycle of heat.

In the examples above, the heat source 110 is a mixture. In an alternative implementation, the heat source 110 can be composed of multiple layers made from inorganic and organic materials. Any suitable number of layers can be provided. The layers may be oriented in any particular order including an inorganic layer positioned between a water layer and an organic layer. In the Alternative, any of the above component layers may be positioned in between another layer. Further, layers may neighbor other layers of similar composition.

In another implementation the heat source 110 may lack the water layer, but include the organic layer and inorganic layer. This type of configuration may be beneficial for a pouch in a pouch assembly to hold the heat source 110.

In another implementation, the heat source 110 may include a wax and water layer each positioned on the periphery of the heat source. In another embodiment, the heat source 110 may include a wax and water layer on each heat source external side, front, and back. In another embodiment, each side, front, and back may each contain a wax layer and a water layer, a wax layer only, or a water layer only.

In another implementation, the composition of the heat source 110 can be tuned to adjust peak temperatures and length of duration as a function of weight percent and overall amount added.

In another implementation, the inorganic and organic layers can be in the same or separate compartments within the housing 120.

In another implementation, the heat source 110 can include a transfer layer such as a gel or a liquid or a solid with high thermal conductivity.

Figure 2:
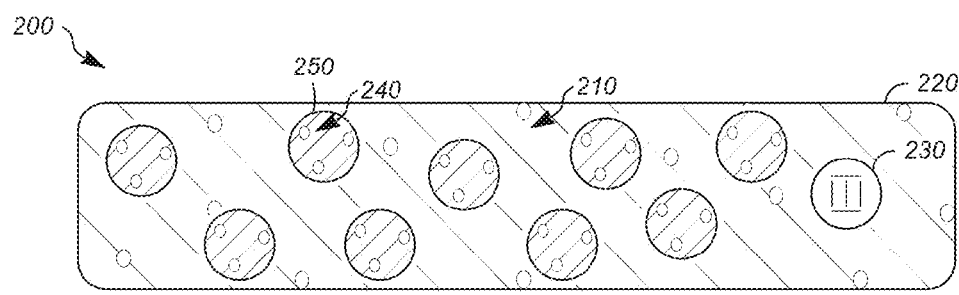
FIG. 2 is an illustration showing a heat pack according to a second example.

FIG. 2 shows a heat pack 200. The heat pack 200 includes a heat source 210 that is contained within a housing 220. An activator 230 is contained in the housing 220 and is in operative contact with the heat source 210. The housing 220 and the activator 230 are as described with respect to the housing 120 and the activator 130 of the heat pack 100.

The heat source 210 includes a first PCM, which is as described with respect to the first PCM of the heat source 110.

The heat pack 200 also includes a thermal storage buffer 240. The thermal storage buffer 240 is as described with respect to the thermal storage buffer of the heat source 110, except that the thermal storage buffer 240 is contained in a thermal storage buffer skin 250. The thermal storage buffer skin 250 can be constructed from polyethylene or another suitable pliable material. The thermal storage buffer skin 250 can be selected to prevent the thermal storage buffer 240 from mixing with the heat source 210. This can, in some implementations, prevent the thermal storage buffer 240 from modifying the heat generating properties of the heat source 210. Use and operation of the heat pack 200 is as described with respect to the heat pack 100.

Figure 3:
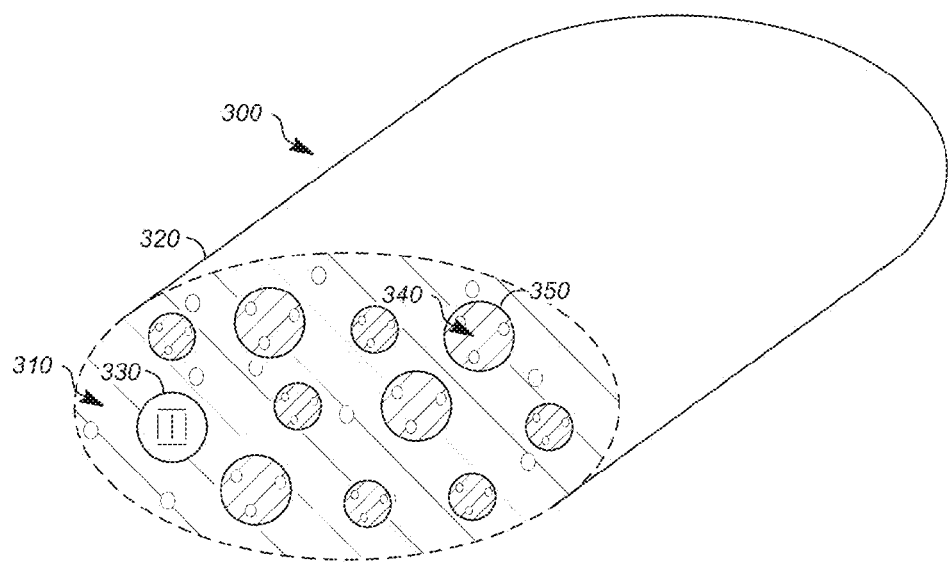
FIG. 3 is an illustration showing a heat pack according to a third example.
Figure 4:
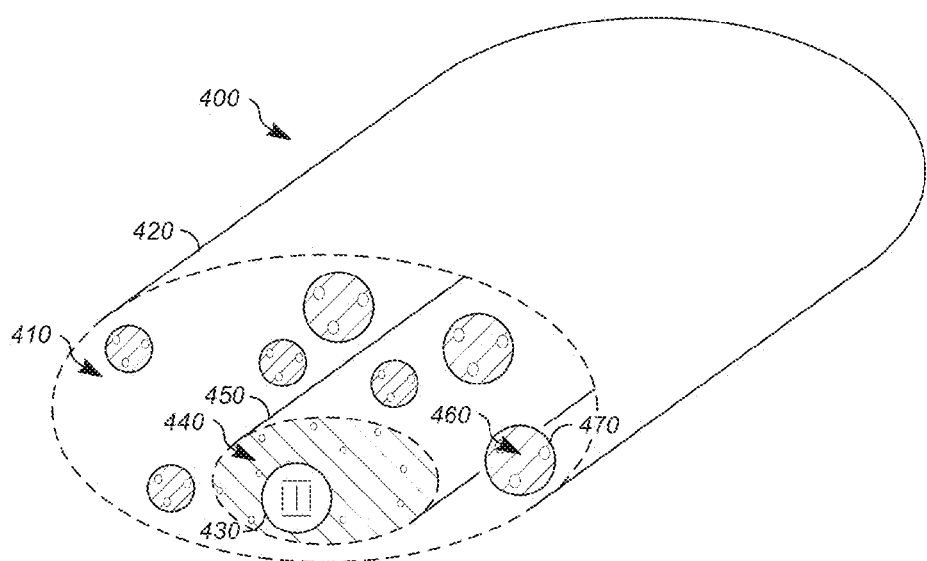
FIG. 4 is an illustration showing a heat pack according to a fourth example.
Figure 5:
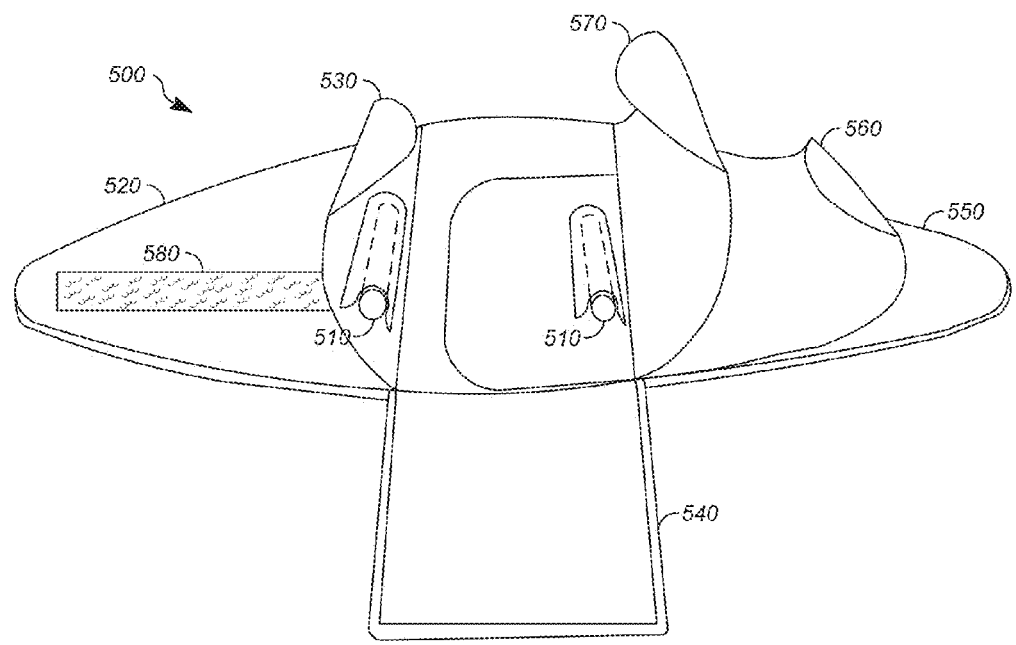
FIG. 5 is an illustration showing an infant warming blanket.

FIGS. 3-4 show heat packs having roughly cylindrical housings that mitigate the effects of mechanical rigidity caused by crystallization of the inorganic PCM.

FIG. 3 shows a heat pack 300 that includes a heat source 310 that is contained within a housing 320. An activator 330 is contained in the housing 320 and is in operative contact with the heat source 310. The housing 320 and the activator 330 are as described with respect to the housing 120 and the activator 130 of the heat pack 100. The heat source 310 includes a first PCM, which is as described with respect to the first PCM of the heat source 110. A thermal storage buffer 340 encapsulated in a thermal storage buffer skin 350 is contained in the housing 320, as described with respect to the thermal storage buffer 240 and the thermal storage buffer skin 250. Use and operation of the heat pack 300 is as described with respect to the heat pack 100.

FIG. 4 shows a heat pack 400. An inert liquid 410 is contained within a housing 420. A thermal storage buffer 460 encapsulated in a thermal storage buffer skin 470 is contained in the housing 320, as described with respect to the thermal storage buffer 240 and the thermal storage buffer skin 250, but can be suspended in the inert liquid 410.

The heat pack 400 can include a heat source 440 that is contained within a flexible heat source container 450. The flexible heat source container 450 is disposed within the housing 420, and can be surrounded by the inert liquid 410. The flexible heat source container 440 can be made from pliable materials polyethylene, rubber, polyvinylchloride, or the like. The flexible heat source container separates the heat source 440 from the inert liquid 410. An activator 430 is contained in the flexible heat source container 450 and is in operative contact with the heat source 440.

Other implementations include features to further mitigate the impact of mechanical rigidity. One example uses a thin or oversized package of sodium acetate to allow a degree of flexibility even after a phase change heat source material becomes a solid and allow enough room for the increased volume change. Another example uses a plasticizer such as ethylene glycol, cellulose, or the like to smooth the phase change and alter the heat source's mechanical properties.

One application for the heat packs described herein is thermoregulation of an infant. The preferred temperature range for an infant is 36 to 37° C. and the acceptable temperature range for an infant is 36 to 38° C. The heat packs described here can provide heat within this temperature range for at least 4 hours. To supply heat to an infant, the heat packs described herein can be utilized in conjunction with an infant warming blanket 500 in which one or more heat packs 510 are placed, as shown FIG. 8. The infant warming blanket 500 includes an outer flap 520, inner flap 530, a leg flap 540, and an outer cover 550. The outer cover 550 includes an insulated layer 560 and an innermost layer 570.

The inner flap 530 can be made from a soft, hypoallergenic material for direct contact with the infant. Materials such as polyester, wool, cotton, cotton flannel, or the like could be used for the inner flap 530. The innermost layer 570 of the outer cover 550 may also be in contact with the infant and can be made from the same or similar materials. The inner flaps 403 and outer cover 407 can be wrapped around the infant and secured using a fastener 580 which may be made out of a soft hook and loop type fastener, buttons, a zipper, or the like.

The outer cover 550 can be fabricated from a material that is waterproof, easy to clean, and abrasion resistant, such as nylon, rip-stop nylon, or polyester. Other materials can be used. The reflective insulated layer 560 beneath the outer cover 550 could be used to reflect heat back toward the infant to aid in heat retention. A reflective insulated layer could also be provided in the inner flap 530. As single material or multiple materials can be used as the reflective insulated layer 560. Suitable insulating and/or reflective materials include cotton, Orlon®, synthetic fill, down, wool, aluminized polyester, polyethylene, and polyester, specifically Mylar®, Reflectix®, and Insul-bright®.

The infant warming blanket 500 can have one of compartments in which one or more heat packs are placed. Any suitable number of compartments can be formed. In one non-limiting example, three compartments are formed in the infant warming blanket For instance, separate compartments can be formed for separate containers having SAT, wax, and water. In an alternative, the water is contained in a pouch or in one or more tubes of any suitable length.

In another implementation, the infant warming blanket can be used with a heat pack in which multiple layers of material are separated, such as by PVC film. For example, the first PCM is disposed in a layer of the heat pack furthest from the interior of the infant warming blanket 550, the second PCM is disposed in a middle layer of the heat pack, and water is disposed in a layer of the heat pack closest to the interior of the infant warming blanket 550. Alternatively, instead of a layered heat pack, each material could be placed in a separate housing an arranged in the same configuration.

Figure 6:
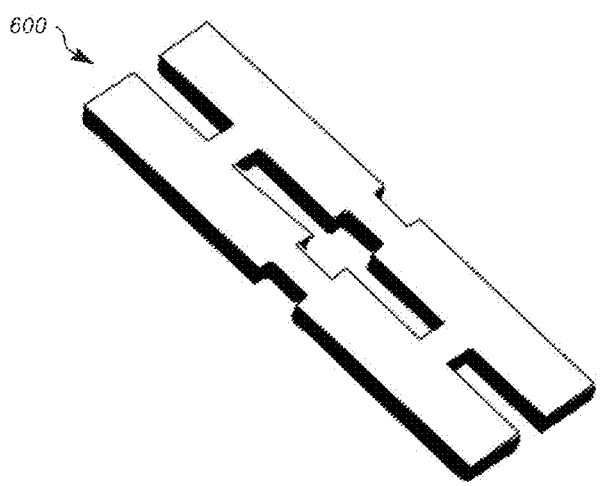
FIG. 6 is an illustration showing a heat pack having a first alternative enclosure.

FIG. 6 shows a system enclosure embodiment configured to evenly distribute heat.

Figure 7:
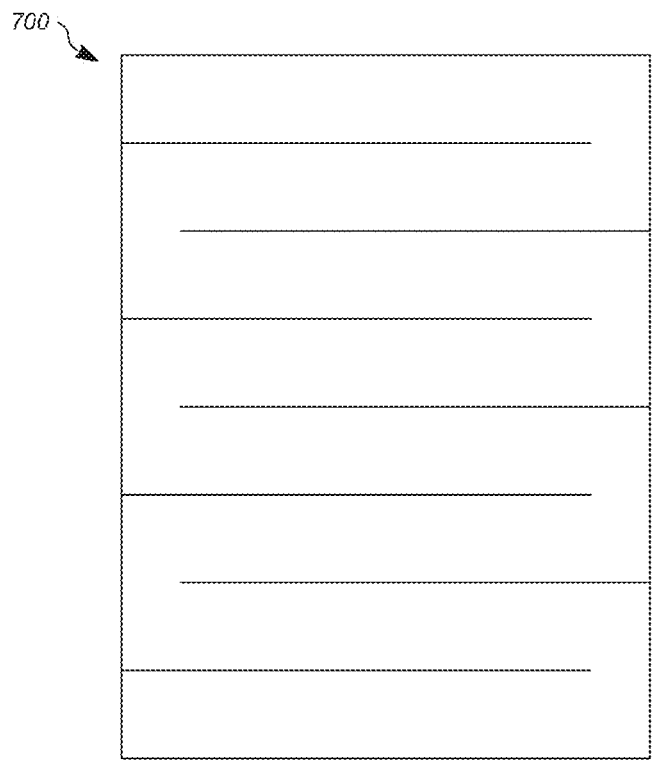
FIG. 7 is an illustration showing a heat pack having a second alternative enclosure.

FIG. 7 shows a system enclosure embodiment configured to regulate the crystallization rate. Interlocked channels 601 slow the propagation of crystallization.

Figure 8:
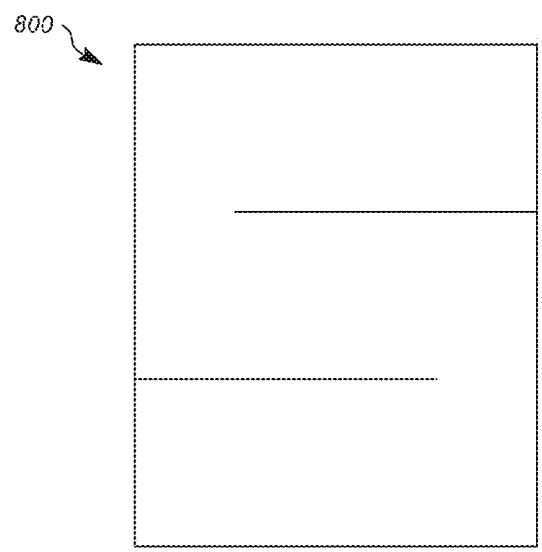
FIG. 8 is an illustration showing a heat pack having a third alternative enclosure.

FIG. 8 shows a system enclosure embodiment with three interlocked channels. These three interlocked channels 601 do not slow down the crystallization rate as much as the embodiment shown in FIG. 7. The interlocked channels 601 also enhance the flexibility of the system enclosure embodiment.

In another implementation, channels of the inorganic PCM and/or the organic PCM can be made in the layers to increase flexibility and/or create more even layers of materials.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the term "polymer" includes "oligomer," "copolymer," "terpolymer," and the like; the description of a group or class of materials as suitable or preferred for a given purpose in connection with the invention implies that mixtures of any two or more of the members of the group or class are equally suitable or preferred; molecular weights provided for any polymers refers to number average molecular weight; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

While the description relates to what are presently considered to be the most practical and preferred embodiments, it is to be understood various modifications or equivalent arrangements are included within the spirit and scope of the appended claims. The scope is to be accorded the broadest interpretation so as to encompass all such modifications and equivalent structures as is permitted under the law.

What is claimed is:

1. A heat pack, comprising:
   a housing;
   a first phase change material (PCM) that is contained in the housing, wherein the first PCM includes sodium acetate;
   a thermal storage buffer that is contained in the housing, wherein the thermal storage buffer includes a second PCM, wherein the thermal storage buffer is in a solution with the first PCM, and the solution includes 75-80% of the first PCM, 10-15% of the thermal storage buffer, and 5-10% water by weight; and
   an initiator in operative contact with the first PCM, wherein activation of the initiator causes crystallization of the first PCM, and the first PCM cooperates with the thermal storage buffer to provide heat at a predetermined temperature range upon crystallization of the first PCM, the predetermined temperature range is from 36 to 44 degrees Celsius the second PCM of the thermal storage buffer has a melting point within the predetermined temperature range.

2. The heat pack of claim 1, wherein the housing is a sealed flexible container.

3. The heat pack of claim 1, wherein the first PCM provides heat at a first temperature that is higher than the predetermined temperature range during crystallization of the first PCM, and the second PCM of the thermal storage buffer moderates the heat generated by the first PCM.

4. The heat pack of claim 1, wherein the second PCM of the thermal storage buffer is an organic material having a melting point within the predetermined temperature range.

5. The heat pack of claim 1, wherein the second PCM of the thermal storage buffer is a wax having a melting point within the predetermined temperature range.

6. The heat pack of claim 1, wherein the second PCM of the thermal storage buffer is a paraffin wax having a melting point within the predetermined temperature range.

7. The heat pack of claim 1, wherein the first PCM includes sodium acetate that provides heat at a first temperature that is higher than the predetermined temperature range during crystallization of the first PCM, and the second PCM of the thermal storage buffer is a paraffin wax having a melting point within the predetermined temperature range.

8. The heat pack of claim 1, wherein the initiator, when activated, provides nucleation sites for the first PCM.

9. The heat pack of claim 8, wherein the initiator includes a stainless steel member and the initiator is activated by physical manipulation of the stainless steel member.

10. A heat pack, comprising:
    a housing in the form of a sealed flexible container;

a first phase change material (PCM) that is contained in the housing, wherein the first PCM includes sodium acetate;

a thermal storage buffer that is contained in the housing, wherein the thermal storage buffer includes a second PCM, the second PCM is paraffin wax, and the thermal storage buffer is contained in a pliable material to prevent the thermal storage buffer from mixing with the first phase change material; and an initiator in operative contact with the first PCM, wherein the initiator includes a stainless steel member that, when activated by physical manipulation of the stainless steel member, provides nucleation sites for the first PCM to cause crystallization of the first PCM, crystallization of the first PCM provides heat at a first temperature, the heat provided by the first PCM melts the second PCM of the thermal storage buffer at a second temperature such that the second PCM of the thermal storage buffer absorbs part of the heat provided by first PCM, and the first PCM cooperates with the thermal storage buffer to provide heat at a predetermined temperature range from 36 to 44 degrees Celsius upon crystallization of the first PCM, the first temperature being above the predetermined temperature range and the second temperature being within the predetermined temperature range.

11. The heat pack of claim 10, wherein the pliable material is polyethylene.

12. A heat pack, comprising:

a housing;

a heat source container that is disposed within the housing;

a first phase change material (PCM) that is contained in the heat source container;

an inert liquid that is contained in the housing such that the inert liquid surrounds the first PCM and such that the heat source container separates the inert liquid from the first PCM;

a thermal storage buffer that is contained in the housing such that the heat source container separates the thermal storage buffer from the first PCM, wherein the thermal storage buffer includes a second PCM; and an initiator disposed within the heat source container in operative contact with the first PCM, wherein activation of the initiator causes crystallization of the first PCM, and the first PCM cooperates with the thermal storage buffer to provide heat at a predetermined temperature range upon crystallization of the first PCM.

* * * * *